United States Patent
Brunner et al.

(10) Patent No.: US 9,616,187 B2
(45) Date of Patent: Apr. 11, 2017

(54) APPARATUS FOR REGULATING A MECHANICAL VENTILATION

(75) Inventors: Josef Brunner, Chur (CH); Marc Wysocki, Chevreves (FR); Thomas Laubscher, Rhazuns (CH)

(73) Assignee: HAMILTON MEDICAL AG, Bonaduz (CH)

( * ) Notice: Subject to any disclaimer, the term of this patent is extended or adjusted under 35 U.S.C. 154(b) by 1285 days.

(21) Appl. No.: 12/162,781

(22) PCT Filed: Jan. 30, 2007

(86) PCT No.: PCT/CH2007/000040
§ 371 (c)(1),
(2), (4) Date: Jul. 30, 2008

(87) PCT Pub. No.: WO2007/085108
PCT Pub. Date: Aug. 2, 2007

(65) Prior Publication Data
US 2009/0007915 A1    Jan. 8, 2009

(30) Foreign Application Priority Data

Jan. 30, 2006 (CH) ..................... 0148/06
Oct. 6, 2006 (CH) ..................... 1597/06

(51) Int. Cl.
*F16K 31/02* (2006.01)
*A61M 16/00* (2006.01)

(52) U.S. Cl.
CPC ... *A61M 16/0051* (2013.01); *A61M 2230/202* (2013.01); *A61M 2230/205* (2013.01)

(58) Field of Classification Search
USPC ............ 128/204.21, 204.18, 204.26, 204.22, 128/204.23; 600/300, 301, 529, 533, 538
See application file for complete search history.

(56) References Cited

U.S. PATENT DOCUMENTS 4,112,938 A * 9/1978 Jeretin ..................... 128/204.23
4,421,113 A * 12/1983 Gedeon et al. .......... 128/204.23
(Continued)

FOREIGN PATENT DOCUMENTS

EP    0347282    12/1989
EP    0753320    * 1/1997 ............ A61M 16/00
(Continued)

OTHER PUBLICATIONS

Laubscher, Thomas P., An Adaptive Lung Ventilation Controller, Jan. 1994, IEEE Transactions on Biomedical Engineering vol. 41 No. 1.*
(Continued)

*Primary Examiner* — Bradley Philips
*Assistant Examiner* — Eric Bryant
(74) *Attorney, Agent, or Firm* — Rothwell, Figg, Ernst & Manbeck, P.C.

(57) ABSTRACT

The invention relates to a device, with which one is to prevent a patient who breathes on Ms own and who desires a lower $CO_2$-partial-pressure than is achieved by the set Ventilation from tiring. It comprises the following means for the regulation of a changing intensity of a mechanical Ventilation: • means for determining a target frequency $RR^{sp}$, • means for determining a spontaneous frequency $RR_{spont}$ • means for comparing the spontaneous frequency $RR_{spont}$ with the target frequency $RR^{sp}$. wherein adapting a Ventilation target value (% MinVol, $V'_{gA}{}^{sp}$) on account of the result of the comparison of the spontaneous frequency $RR_{spont}$ with the target frequency $RR^{sp}$ and • means for adapting the parameters determining the intensity of the Ventilation, on account of the Ventilation target value (% MinVol, $V'_{gA}{}^{sp}$). This so-called pump support System (PSS) is activated (PSS on) when the patient breathes in an adequately spontaneous manner (Criterion 1). With an insuf- (Continued)

ficient individual activity of the patient, his behavior is taken as a basis for the control of the regulation. The control or regulation of the Ventilation is assumed by a fixed setting of a Ventilation target value (% MinVol), or a $CO_2$-controller, as soon as the patient breathes in a manner which is not spontaneous enough.

29 Claims, 4 Drawing Sheets (56) References Cited

U.S. PATENT DOCUMENTS

| | | | |
|---|---|---|---|
| 5,103,814 A | | 4/1992 | Maher |
| 5,107,830 A | * | 4/1992 | Younes .................... 128/204.18 |
| 5,365,922 A | * | 11/1994 | Raemer ................... 128/204.23 |
| 5,388,575 A | | 2/1995 | Taube |
| 5,402,796 A | | 4/1995 | Packer et al. |
| 5,447,523 A | * | 9/1995 | Schaldach ....................... 607/19 |
| 5,660,170 A | | 8/1997 | Rajan |
| 5,738,090 A | | 4/1998 | Lachmann |
| 5,752,509 A | | 5/1998 | Lachmann |
| 5,931,160 A | * | 8/1999 | Gilmore ............... A61M 16/00 128/204.18 |
| 5,937,854 A | | 8/1999 | Stenzler |
| 6,000,396 A | * | 12/1999 | Melker et al. ........... 128/204.21 |
| 6,071,237 A | | 6/2000 | Weil et al. |
| 6,116,241 A | | 9/2000 | Huygen |
| 6,471,658 B1 | * | 10/2002 | Daniels et al. ................ 600/538 |
| 6,532,957 B2 | * | 3/2003 | Berthon-Jones ......... 128/204.21 |
| 6,532,959 B1 | * | 3/2003 | Berthon-Jones ......... 128/204.23 |
| 6,557,554 B1 | * | 5/2003 | Sugiura ................... 128/204.18 |
| 6,578,575 B1 | | 6/2003 | Jonson |
| 6,581,597 B2 | * | 6/2003 | Sugiura ................... 128/204.21 |
| 6,668,829 B2 | * | 12/2003 | Biondi et al. ............ 128/204.21 |
| 6,951,217 B2 | * | 10/2005 | Berthon-Jones ......... 128/204.23 |
| 7,077,132 B2 | * | 7/2006 | Berthon-Jones ......... 128/204.23 |
| 7,520,279 B2 | * | 4/2009 | Berthon-Jones ......... 128/204.21 |
| 2001/0007256 A1 | * | 7/2001 | Sugiura ................... 128/204.21 |
| 2004/0074497 A1 | | 4/2004 | Berthon-Jones et al. ........................ 128/204.23 |
| 2004/0173212 A1 | * | 9/2004 | Berthon-Jones ......... 128/204.18 |
| 2004/0206355 A1 | | 10/2004 | Berthon-Jones et al. ........................ 128/204.23 |
| 2004/0231670 A1 | * | 11/2004 | Bassin ..................... 128/204.18 |
| 2005/0133032 A1 | * | 6/2005 | Berthon-Jones et al. ........................ 128/204.23 |
| 2006/0065270 A1 | * | 3/2006 | Li ..................... A61M 16/0057 128/204.18 |
| 2006/0150974 A1 | * | 7/2006 | Berthon-Jones ......... 128/204.21 |
| 2007/0163590 A1 | * | 7/2007 | Bassin ..................... 128/204.23 |
| 2008/0035147 A1 | * | 2/2008 | Kirby et al. ............. 128/204.21 |
| 2008/0314385 A1 | * | 12/2008 | Brunner et al. ......... 128/204.23 |

FOREIGN PATENT DOCUMENTS

| | | |
|---|---|---|
| FR | 2356408 | 1/1978 |
| WO | WO 0066210 | 9/2000 |

OTHER PUBLICATIONS

Cairo, J.M. and Pilbeam, S.P. "Mosby's respiratory care equipment," 2004 Mosby, Us, St Louis 288730, XP002427992 p. 477-p. 494; figures 12.44-12.54.

* cited by examiner

APPARATUS FOR REGULATING A MECHANICAL VENTILATION

CROSS-REFERENCE TO RELATED APPLICATIONS

This application is a National Stage under 35 U.S.C. §371 of International Application No. PCT/CH2007/000040, filed Jan. 30, 2007, which claims the benefit of Swiss Patent Application No. 148/06, filed Jan. 30, 2006, and Swiss Patent Application No. 1597/06, filed Oct. 6, 2006, the entirety of each of which is incorporated by reference.

The invention relates to an apparatus for regulating a mechanical ventilation.

$CO_2$ produced in the body of a patient by way of metabolism, is transported into the lung with the blood and is breathed out there. The higher the $CO_2$-production of the body, the higher must the alveolar ventilation be, in order to keep the arterial $CO_2$-partial-pressure constant. An increase of the alveolar ventilation is achieved with mechanical ventilation by way of a recruitment of inactive lung shares or by way of increasing the minute volume.

Minute volume (MV) is indicated as the volume of air which is breathed in and out again in one minute. The minute volume may be computed from the respiratory frequency and the breath volume. The breath volume is the quantity of air which is breathed in per breath.

The measured minute volume thereby is dependent on the respective person and his circumstances, i.e. his exertion, his constitution, his health condition, his volume and his body size. The minute volume with bodily exertion may increase by 3-4 times. Furthermore, there are unhealthy conditions, such as fever, lung embolism, metabolic acidosis and disturbance of the respiratory centre, which may increase the MV. Hyperventilation of course entails an increased minute volume.

The minute volume during sleep, sinks to below the daily resting values. When taking sedatives, a reduction of the MV occurs with a higher dose. The expenditure of oxygen may lead to a reduction of the MV with people who are chronically adapted to an increased, arterial $CO_2$-partial-pressure.

A minute volume according to the person may be calculated from details on this person. A minute volume calculated in this manner is indicated as a 100% minute volume. Deviations in the minute volume of this person may then relate to this 100% Min Vol. This percentage minute volume (% Min Vol) is therefore a variable, which is related to the minute volume corresponding to the respective person. These values, in contrast to the nominal value of the minute volume or the alveolar ventilation, provide relative information concerning the person, as to whether the person is greatly or weakly ventilated.

With a computation of the necessary total ventilation, amongst other things, one may take into account the fact that on ventilation, apart from the effective alveolar ventilation, a ventilation of the alveolar dead space (alveoli not circulated with blood) and of the serial dead space (tubus and upper airways) is effected, said ventilation not being effective. The minute ventilation (MV) is composed of the total alveolar ventilation ("gross alveolar ventilation" $V'_{gA}$) and the serial dead space ventilation. $V'_{gA}$ is composed of the effective alveolar ventilation ($V'_A$) and of the alveolar dead space ventilation ($V'_{dA}$). The serial dead space ventilation is the product of the ventilation rate times the serial dead space ($V_{dS}$).

The benefits and risks are to be weighed up with the mechanical ventilation of the lungs of a patient. The ventilation must be increased in order to reduce the $CO_2$-content in the blood. The frequency and the ventilation pressure (the volume) may be increased in order to increase the ventilation volume. Each increase of these parameters however entails risks.

An apparatus for the spontaneous ventilation with a variable breathing aid is known from EP-A 0 347 282. This apparatus has the aim of preventing an unnecessary tiring of the patient by way of keeping the respiratory frequency constant. This apparatus produces a ventilation control signal on account of a pressure sensor in the insufflation conduit. The supplied control signal is representative of the determined change of the respiratory frequency with respect to a predefined reference respiratory frequency. A positive pressure level is adapted on account of this control signal, so that the respiratory frequency remains essentially constant at the value of the predefined reference respiratory frequency.

If the respiratory frequency assumes a value above a predefined range, the breathing support is increased, in order to relieve the patient from the increased work for breathing, until the respiratory frequency has returned back into the preselected frequency range. If the respiratory frequency lies below this range, the breathing support is reduced, until the patient has increased the respiratory frequency to such an extent, that it lies in the predefined frequency range.

The disadvantage with this device is the fact that the rate is set in a fixed manner. If the physician sets the rate too low, then one ventilates with a high pressure. If however the rate is set too high, the patient obtains too little support and tires despite this.

It is therefore the object of the invention to provide a device and a method, with which one may control a ventilator in a manner such that the ventilated patient is ventilated as optimally as possible. The object in particular lies in preventing a patient who breathes independently and wishes $CO_2$-partial-pressure which is lower than is achieved by way of the set ventilation, from tiring.

According to the invention, this object is achieved by a device according to claim 1.

Such a device for the regulation of an intensity of a mechanical ventilation comprises the following means:
means for determining a target frequency $RR^{sp}$,
means for determining a spontaneous frequency $RR_{spont}$,
means for comparing the spontaneous frequency $RR_{spont}$ with the target frequency $RR^{sp}$.

This device according to the invention is characterised by means for adapting a ventilation target value by way of the result of the comparison of the spontaneous frequency $RR_{spont}$ with the target frequency $RR^{sp}$ and
means for adapting the parameters determining the intensity of the ventilation, by way of the ventilation target value.

The device according to the invention is characterised preferably by means for setting the target rate $RR^{sp}$ by way of the adapted ventilation target value (% MinVol, $V'_{gA}{}^{sp}$). Very advantageously, the device also comprises means for setting the ventilation pressure or the breath volume by way of the adapted ventilation target value (% MinVol, $V'_{gA}{}^{sp}$).

If these means are present, it is then preferred for the device to have a controller, which is suitable for matching the parameters determining the intensity. Such parameters in particular are the ventilation pressure or the breath volume on the one hand, and the ventilation frequency ($RR^{sp}$, $RR_{IMV}$) on the other hand. Such a matching is usefully effected on account of patient parameters, which influence the optimisation of pressure and rate.

Furthermore, this device usefully comprises means for regulating or activating the ventilator according to the intensity of the ventilation which is determined by way of the above means, so that the patient may also be mechanically ventilated accordingly.

Thereby, usefully different deviations of the spontaneous frequency $RR_{spont}$ from the predefined target value $RR^{sp}$ are tolerated, depending on the goal of the therapy and the ventilation target value (or currently set % MinVol).

This tolerated deviation is in particular-advantageously dependent on the goal of the therapy. It may, depending on the goal of the therapy, be defined as a constant number of breaths per unit of time, or depending on a ventilation intensity or a ventilation target value.

In the case that a normal withdrawal is defined as a therapy goal, and the tolerance range is defined as the number of breaths per minute, usefully between maximal 3 and maximal 8, particularly preferred between 4.5 and 5.5 breaths per minute should be tolerated. With a forced withdrawal however, these values increase to values between maximal 7 and maximal 15, particularly preferred between 9 and 11 breaths per minute.

If the tolerance range is defined depending on the supplied % MinVol, then a tolerance range which may be defined as the current % MinVol setting divided by a divisor may be considered as being useful. The number value of the divisor preferably lies in the region of 12 to 33, particularly preferably from 18 to 22. The tolerance range dependent on % MinVol is larger with a forced withdrawal than with a strategy which demands less of the patient.

This device has the advantage that the ventilation may be automatically adapted to the requirement of the patient, without a measurement of the arterial $CO_2$-partial-pressure being necessary for this. The body of the patient is used as a subjective $CO_2$-sensor.

Such a device may therefore complement the ventilator to the extent that this prevents a fatigue of the patient, independently of whether a ventilator is geared to a $CO_2$-measurement or not.

A ventilator may however have a regulation or control of the ventilation which is geared to a measurement which is representative of the arterial $CO_2$-partial-pressure.

Such a ventilator of course serves for the mechanical ventilation of the lung of a patient with the goal of keeping the arterial $CO_2$-partial-pressure of the patient in a target range by way of a continuously adapted regulation. This ventilator usefully includes the means for mechanical ventilation of the patient and possibly also the sensors required for a perfect functioning of the device. It however includes at least one electronic data processing unit with
  inputs for signals of sensors for readings with regard to the $CO_2$-partial-pressure in the blood of the patient, and for signals with regard to the ventilation parameters and other setting values of a ventilator,
  outputs for output signals, by way of which output signals, the ventilation parameters are set in the ventilator.

This data processing device furthermore requires memories with data which may be called up.

In one advantageous embodiment of the invention, such data includes
  characteristic line pairs which are stored in the memories, said characteristic line pairs comprising a first characteristic line defining a maximal arterial $CO_2$-partial-pressure $PaCO_2$, and at a distance to this, a second characteristic line defining a minimal $PaCO_2$, by way of which three regions are defined depending on a ventilation intensity, specifically a first region "too high", a second region "normal" between the characteristic lines, and a third region "too low",
  and current values as well as values preceding these, with regard to changing ventilation parameters, said values being stored in the memories.

A single characteristic line may be stored instead of characteristic line pairs, and a correction factor for the correction of the ventilation target value which is defined depending on the deviation of a current reading for the arterial $CO_2$-partial-pressure $PaCO_2$ from this characteristic line, may be provided. The larger the distance between the reading and the characteristic line, the larger is also the correction of the ventilation target value. The correction factor may further be fixed depending on the direction of the deviation, as well as depending on the current intensity of the ventilation or the current ventilation target value. An effect comparable to both characteristic lines may be achieved by way of this, wherein added to this is the fact that the ventilation target value is practically continuously changed, in order to bring the current readings to the optimised value represented in the characteristic line, and is not merely changed until these readings come to lie in the region between the two characteristic lines.

One input possibility with this apparatus is advantageously the therapy target, specifically
  normal withdrawal or
  forced withdrawal.

Again, different characteristic line pairs or characteristic lines and correction factors are assigned to these therapy goal settings. The course of the two characteristic lines or the characteristic line or the correction factor is then optimised according to the therapy goal Advantageously, a trigger signal which displays the patient's individual activity is taken into account with the computation of the output signals, so that one ventilates according to the wishes of the patient. Furthermore, the computation unit is programmed in such a manner as to determine a spontaneous rate $RR_{spont}$ from a number of acquired trigger signals per time unit. This allows one to ascertain how active the patient is.

A device for regulating a mechanical ventilation of the lung of a patient, or for regulating an apparatus for ventilating the lung, said device being geared to a $CO_2$-reading, thanks to the following means, may achieve a continuously adapted $CO_2$-partial-pressure in the arterial blood of the patient, which is fitting for the patient:
  means for regulating or activating the ventilation for achieving a predefined $CO_2$-partial-pressure.
These means realise the ventilation of the patient e.g. in a conventional manner.
  means for determining a target frequency $RR^{sp}$ as well as for determining a mechanical frequency $RR_{IMV}$ for the ventilation, said mechanical frequency being determined in dependence on the target frequency $RR^{sp}$ and, as the case may be, of a spontaneous frequency $RR_{spont}$.
A mechanical frequency $RR_{IMV}$ is necessary, so that the ventilator steps in when the patient has not triggered the breath himself. The evaluation of the spontaneous frequency and the target frequency is necessary in order to be able to compare these.
  means for comparing a spontaneous frequency $RR_{spont}$ with the target frequency $RR^{sp}$ and
  means for adapting a ventilation target value by way of a deviation of the spontaneous frequency $RR_{spont}$ from the target frequency $RR^{sp}$ and means for adapting the parameter determining the intensity of the ventilation by way of the ventilation target value.

The adaptation of the factors determining the intensity of the ventilation on account of the adapted ventilation target value serves for relieving the patient who breathes too rapidly.

In one embodiment, the means for adapting the ventilation target value are designed in a manner such that they multiply a target value for the total alveolar ventilation $V'_{gA}{}^{SP}$ by way of a factor larger than 1 should $RR_{spont}$ lie above the computed target frequency $RR^{SP}$ by a certain number of breaths per minute. Usefully, simultaneously with the increase of the target volume $V'_{gA}{}^{SP}$, they may also lower a target value for the ingoing, representative reading $PaCO_2{}^{REP}$ for $PaCO_2$. In another embodiment, the intensity of the ventilation is regulated via the % MinVol as a ventilation target value.

The treatment level which is the intensity of the ventilation may e.g. be defined as $RR_{IMV}*(PEEP+P_{insp})$. Thereby, $RR_{IMV}$ is the mechanical frequency of the ventilation, PEEP the residual pressure (positive pressure with respect to the atmosphere) during expiration, and $P_{insp}$ the additional pressure during inspiration. This intensity is then specified e.g. as $cmH_2O*bpm$ (bpm=breaths per minute), and lies between 0 and 1500. The intensity of the ventilation may however also be defined in a different manner, e.g. as PIP (peak inspiratory pressure), $PEEP+P_{insp}$, $Pinsp*RR_{IMV}$ or likewise. Usefully, the intensity of the ventilation is defined by the product of a pressure factor and a frequency factor, or of a volume factor and of a frequency factor.

The task of ventilating a patient according to requirements, is achieved by a method for the regulation of a mechanical ventilation of the lungs of a patient for achieving a continuously adapted $CO_2$-partial-pressure in the blood of a patient, which comprises the following method steps, or by way of an apparatus with this purpose which implements the following method steps:

in the case that a $CO_2$-reading is present: regulating the ventilation for achieving a predefined $CO_2$-partial-pressure, as the case may be, with a known method. A certain intensity of the ventilation results by way of this.

determining a target frequency $RR^{sp}$ and a spontaneous frequency $RR_{spont}$, and as the case may be, a mechanical frequency $RR_{IMV}$ for the ventilation, wherein the mechanical frequency is dependent on the target frequency $RR^{sp}$ and, as the case may be, on a spontaneous frequency $RR_{spont}$.

comparison of the spontaneous frequency $RR_{spont}$ with the target frequency $RR^{sp}$, and adapting a ventilation target value on account of a deviation of the spontaneous frequency $RR_{spont}$ from the target frequency $RR^{sp}$ adapting the parameters determining the intensity of the ventilation on account of the ventilation target value.

This control loop serves for the prevention of a fatigue of a self-breathing patient who desires a more intensive ventilation, than results from the prior regulation or control of the ventilation.

Usefully, a target value for the total alveolar ventilation $V'_{gA}{}^{SP}$ is multiplied by a factor larger than 1 for adapting the intensity of the ventilation, in the case that $RR_{spont}$ lies above the computed target frequency $RR^{sp}$ more than a certain number of breaths per minute. Accordingly, with a regulation of the ventilation above the % MinVol, this % MinVol is multiplied by a factor larger than 1.

In the case that the basic regulation of the ventilation is geared to a reading which is representative of the $PaCO_2$ of the patient ($PaCO_2{}^{REP}$), then for the adaptation of the intensity of the ventilation, usefully simultaneously with the enlargement of $V'_{gA}{}^{SP}$ or % MinVol, a target value for the ingoing, representative reading $PaCO_2REP$ for $PaCO_2$ is reduced. This ensures that a basic regulation directed to a $CO_2$-reading does not work against this correction on account of the respiration rate. The range for a normal $PaCO_2{}^{REP}$ is thus extended to the bottom by way of lowering the characteristic line for the minimal $PaCO_2{}^{REP}$, or shifted to the bottom by way of lowering the single characteristic line or both characteristic lines.

With a device with which a $CO_2$-controller is present, as soon as this is active, the respective, current representative reading $PaCO_2{}^{REP}$ is also incorporated into a regulation of the intensity of the ventilation. This is advantageously effected in that the reading is compared to one or both characteristic lines, and the intensity of the ventilation is changed in a manner such that the representative reading $PaCO_2{}^{REP}$ tendentially approaches the single characteristic line or is to get between the two characteristic lines. With such a device, the means for adapting the intensity on account of the comparison of the spontaneous rate to the target rate partly assumes the regulation of the intensity of the ventilation instead of the $CO_2$-controller. These means further have the effect that at latest, with the adoption of the control by the $CO_2$-controller, the individual characteristic line or both characteristic lines are shifted to such an extent, that the lowered current, representative reading $PaCO_2{}^{REP}$ lies on the individual characteristic line or centrally between the two characteristic lines. Thereafter, the $CO_2$-controller again regulates the intensity of the ventilation.

Advantageously, first and second means for determining or adapting a ventilation target value are present. Means for switching-over from the first means to the second means for adapting the ventilation target value, switch over on account of certain criteria. These criteria indicate whether the patient breaths in an adequately spontaneous manner or not.

Advantageously, with a spontaneously breathing patient, the means for adaptation of the ventilation target value on account of the comparison of the spontaneous rate $RR_{spont}$ to the target rate $RR^{sp}$ assume the adaptation of the ventilation target value in accordance with the patient, since these react to the individual reaction of the patient. For this reason, with these, one may regulate the ventilation such that the patient is optimally ventilated in an individual manner and without $CO_2$-measurement. If the patient however breaths in a too little spontaneous manner, then a predefined setting of the ventilation target value is used as a basis for the respiration, or a $CO_2$-controller assumes the adaptation of the ventilation target value on account of a reading.

The means for adapting the ventilation target value on account of the comparison of the spontaneous- and target rate are advantageously activated continuously and by way of this adapt the ventilation target value to the requirements of the patient in breaths.

Figure 1:
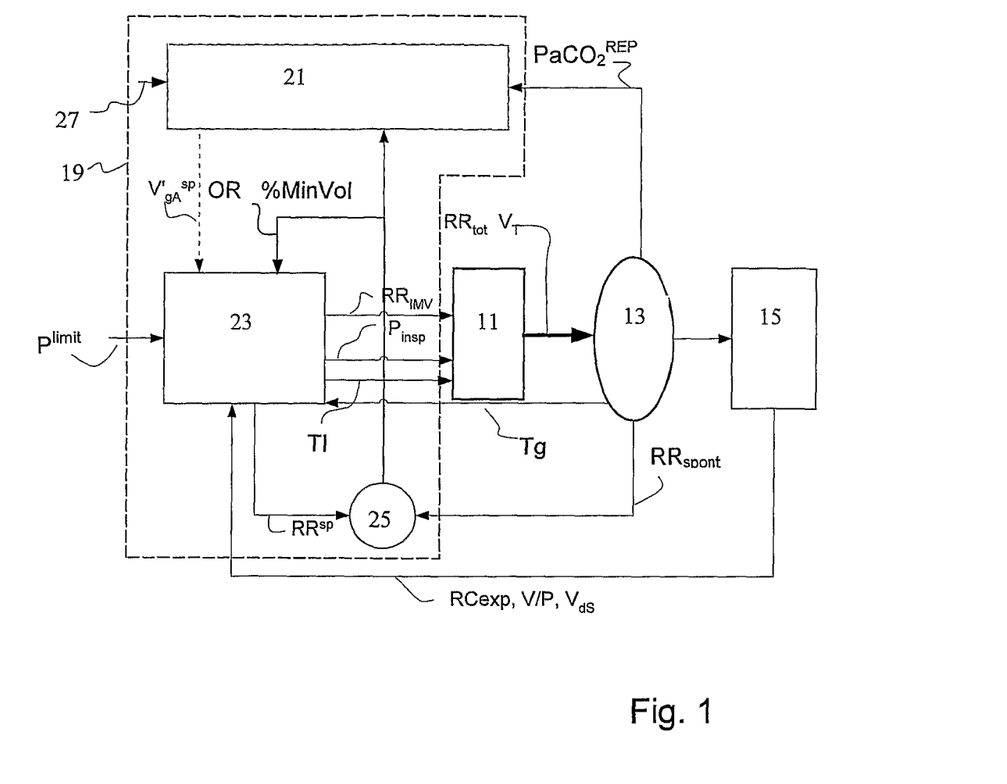
FIG. 1 shows a sketch with a schematically represented electronic circuit, a ventilation device and a patient.

In many cases, the regulation of the ventilation according to the invention is carried out with an apparatus which takes into account a $CO_2$-reading. Such an apparatus is schematically represented in FIG. 1 and is described hereinafter. The teaching according to the invention described in this context indeed has the advantage that it also makes do without $CO_2$-measurement when the patient breathes in a spontaneous manner. With ventilators for patients breathing in a non-spontaneous manner however, the integration of a $CO_2$-controller is useful.

The sketch represented-in-FIG. 1 apart from an electronic circuit 19 comprises a ventilation device 11 with which a patient 13 may be ventilated. The electronic circuit may comprise a $CO_2$-controller 21. The device according to the invention may however also make do without this $CO_2$-controller 21, and utilises the reaction of the spontaneously breathing patient, in order to draw conclusions on a ventilation matched to the patient and to approximate this.

The patient is monitored with various sensors. A trigger signal Tg is used in the case that the patient actively breathes in. In any case, these sensors provide a value for the respiratory frequency $RR_{spont}$ triggered by the patient (or readings and setting values from which these values may be derived). These sensors, with an apparatus provided with a $CO_2$-controller, provide a value $PACO_2^{REP}$ which is representative of the arterial $CO_2$-partial-pressure. Furthermore, they may provide the flow of the respiratory gases, the pressure of the respiratory gases and the $CO_2$-concentration in the respiratory gases $FCO_2$. From $RR_{spont}$ of these last two values, one may calculate the expiratory time constant of the patient, the ratio V/P of the respiratory volume V to the ventilation pressure P, as well as the serial dead space $V_{dS}$ of the patient lung, in a patient model 15.

The circuit 19 regulates the mechanical ventilation which is effected by the ventilator 11, on account of these signals and computation values.

The basis of the circuit 19 is an "ALV-controller" or an "ASV-controller" (AC) 23. An "ALV-controller" processes a target value for the total alveolar ventilation. An "ASV-controller" processes a target value as % MinVol. As a second member, a "pump support system" (PSS) according to the invention is present, which is indicted at the reference numeral 25. A $CO_2$-controller 21 may be present as a third member, which computes the target value for the ventilation from a representative reading for the arterial $CO_2$-partial-pressure as soon as the PSS may not assume its task. The PSS may not assume its task only when the patient breathes in too low a spontaneous manner.

The $CO_2$-controller (CC):

If a ventilation target value evaluation may not be carried out on account of the PSS, then either a safety setting is set up, or a regulation by way of a $CO_2$-controller (CC).

The CC 21 on account of an input (lung parameter/patient parameter/therapy goal 27) which defines the patient, in particular his lung condition, his disease or the treatment goal, on account of the representative reading $PaCO_2REP$ for the arterial $CO_2$-partial-pressure of the patient, and from the present, total alveolar ventilation, calculates the total alveolar ventilation which this patient requires. The computed value for this total alveolar ventilation $V'_{gA}{}^{sp}$ (gross alveolar ventilation) also includes the ventilation of the alveolar dead space $V'_{dA}$. In place of this total alveolar ventilation $V'_{gA}{}^{sp}$, one may also compute the percent-minute volume % MinVol from the CC. The CC presents this ventilation target value to the ALV-controller or ASV-controlled, known from publications of the applicant, as a basis for the computation of the ventilation frequency and the ventilation pressure. In this context, the following description in which one only refers to the total alveolar ventilation $V'_{gA}{}^{sp}$ also implies % MinVol.

The representative reading is evaluated in that the end-tidal $CO_2$-content of the airway gases is measured by way of infrared absorption. This end-tidal $CO_2$-partial-pressure $P_{et}CO_2$ represents the arterial $CO_2$-partial-pressure $PaCO_2$ relatively well, as long as the alveolar dead space is small. With a larger alveolar dead space VdA, this measured value may be multiplied by a correction factor. Such a correction factor may e.g. be evaluated with the help of a blood gas analysis and the $CO_2$-Kapnogram measured at the same time (see e.g. Brunner J X, Wolff G, Pulmonary Function Indices in Critical Care patients, Berlin, Springer publishing house 1988, pages 37 to 39).

The computation of the necessary ventilation by way of the CC is based on the representative value for the arterial $CO_2$-partial-pressure and the input 27 (lung parameter/patient parameter/therapy goal). The CC assesses the representative value $PaCO_2^{REP}$ differently in accordance with the input 27 (lung parameter/patient parameter/therapy goal). The assessment is effected on account of three regions for $PaCO_2^{REP}$, so that the value may be graded as "too high", "too low" or "normal". By way of changing the target value $V'_{gA}{}^{sp}$ for the ventilation, one attempts to be able to shift the arterial $CO_2$-partial-pressure in the direction of the region "normal".

As to what is to be assessed as "normal", is dependent on the lung parameter/patient parameter and on the therapy goal inputted by the operating personnel. A different assessment basis is applied depending on this or these input parameters 27.

Four bases for assessment are represented in the FIGS. 2 to 5. These figures show graphic representations of functions. The intensity of the ventilation is plotted on the x-axis of these representations. This intensity (treatment level) is the product of the mechanical respiration rate $RR_{IMV}$ times the sum of the end-tidal expiration pressure PEEP (positive EndExpiratory pressure) and the insufflation pressure over PEEP:$P_{insp}$. This scale runs from 0 to 1500 $cmH_2O$*bpm. The value $PaCO_2REP$ (or "$PaCO_2$") representative of the arterial $CO_2$-partial-pressure is plotted on the y-axis. This pressure may as a rule not increase above a value of 65 mmHg. This value should as a rule also not fall below a value of 33 mmHg, since otherwise the ventilation is operated too intensively. With normal patients without ARDS, COPD or brain injury, at least 38 is to be assumed as a lower value and maximally 65 as an upper value. With brain injuries, the normal region 22 is even tighter and to be understood as being lower between 33 and 400 mmHg. With ARDS-patients, a normal region 33 lies between 40 and 65 mmHg. With COPD-patients tendentially even greater between 45 and 65 mmHg. The specified values are merely provisional assumptions which need to be confirmed or corrected by way of experimental trials.

Each assessment basis has three regions "too high" 35, "normal" 33 and "too low" 31. These regions are separated by the characteristic lines 37, 39. The upper characteristic line 39 marks the upper limit for the $CO_2$-partial-pressure, the lower characteristic line 37 the lower limit for the $CO_2$-partial-pressure. Thus the normal region 33 lies between these characteristic lines. If the representative value $PaCO_2^{REP}$ (or "$PACO_2$") falls in this region, then a change in the target value $V'_{gA}{}^{SP}$ is carried out.

These characteristic lines do not run parallel over the whole x-axis, for optimising the treatment intensity and the $CO_2$-partial-pressure of the patient. The characteristic line increases from an intensity of the ventilation which is necessary for the survival of the patient (i.e. from a limit value between 250 and 350 $cmH_2O$*bpm). This means:

With a normal patient (FIG. 2), with a ventilation intensity of 300 $mmH_2O$*bpm, values for $PaCO_2REP$ which lie in the region of 41.4 to 49 are considered as being alright. The more the intensity however increases, be it due to an increase of the mechanical respiration rate $RR_{IMV}$, due to an increase of the PEEP and/or due to an increase in the inspiratory pressure $P_{insp}$, the upper limit and the lower limit of the normal region 33 is lifted. The normal region therefore with an intensity of 1500 $cmH_2O$*bmp ends at a level of at least 55 (characteristic line 37) and at the most 65 mmHg (characteristic line 39). The characteristic lines with the specified, linear scales are straight lines and with an intensity of 0 end at the values 38 (characteristic line 37) and 45 mmHg (characteristic line 39).

Figure 3:
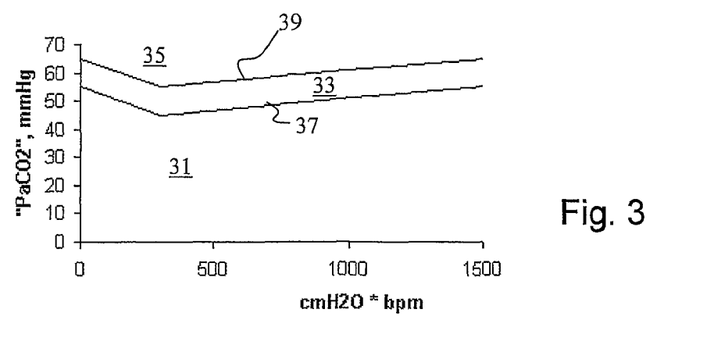
FIG. 3 shows a diagram with two characteristic lines for COPD-patients.

The assessment basis for a COPD-patient is graphically represented in FIG. 3. The assessment basis for an ARDS-patient is graphically represented in FIG. 4. The characteristic lines 37, 39 with both representations have a lowest value at 300 $cmH_2O$*bpm. This means below this limit value of the ventilation intensity, the region for values for $PaCO_2^{REP}$ are to be graded as normal, is lifted with an increasing intensity. This course of characteristic lines has the effect that the reduction of the intensity as well as the increase of the intensity below this limit value must tendentially have a greater extent, in order to correct a $PaCO_2^{REP}$-value outside the normal region 33, than is the case with an intensity above this limit value. For this reason one corrects in a finer manner above this limit value than below the limit value.

Figure 4:
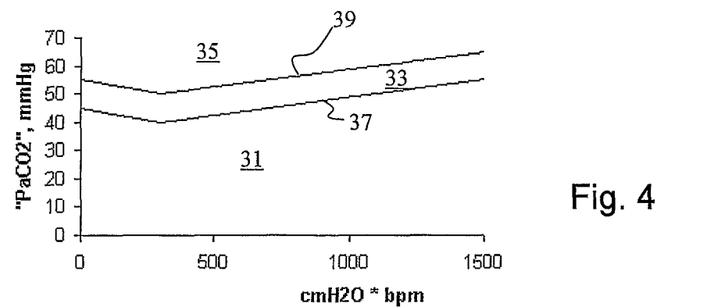
FIG. 4 shows a diagram with two characteristic lines for ARDS-patients.
Figure 5:
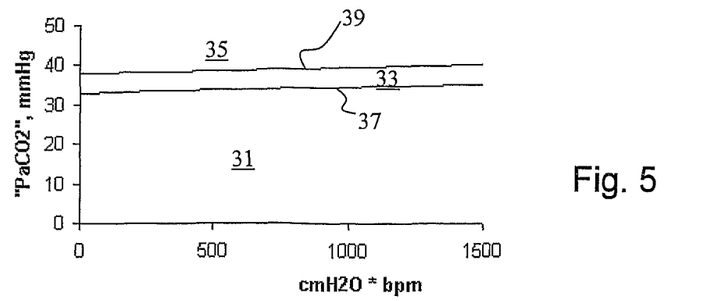
FIG. 5 shows a diagram with two characteristic lines for patients with a brain injury.

With ARDS-patients furthermore, one strives for a lower $CO_2$-partial-pressure than with COPD-patients. With brain injuries, one takes characteristic lines running in a flat manner which delimit a relatively tight region with a relatively low $CO_2$-partial-pressure as a normal region 33.

The extended ALV- or ASV-controller (AC):—

The AC on account of the ventilation target value predefined by the CC or the PSS computes a target value $RR_{sp}$ for the respiration rate, and an inspiratory pressure $P_{insp}$. The AC on account of the serial dead space and the expiratory time constant of the respective patient, with the formulae of Otis and Mead, computes the respiratory frequency and the tidal volume necessary for achieving the predefined target value $V'_{gA}{}^{SP}$ or % MinVol. This AC is indicted here as extended, since, differently to the known ALV-controller, it also computes with the Mead formula.

The actual respiration rate $RR_{tot}$ with a passive patient is equal to the machine respiration rate $RR_{IMV}$, and this is equal to the target value $RR_{sp}$ for the respiration rate. An active patient on the other hand breathes himself, and by way of this activates the support by the ventilator himself. By way of a breath triggered by the patient, the actual respiration rate $RR_{tot}$ is increased with respect to the machine respiration rate $RR_{IMV}$. This increase is recognised by the AC, and it sets the machine respiration rate $RR_{IMV}$ lower that the target value $RR^{sp}$, so that the patient may trigger the breath himself. The higher the actual respiration rate $RR_{tot}$ lies above the machine respiration rate, the more this machine respiration rate approaches a minimal rate. The target rate $RR_{sp}$ on the other hand remains at the level which is always computed afresh on account of the setting of the CC.

The AC 23 according to FIG. 1, depending on the activity of the patient, selects the formula according to Otis or the formula according to Mead for computing the tidal volume $VT^{sp}$ and the appropriate frequency $RR^{sp}$. Subsequent regulators regulate $RR_{IMV}$ and $P_{insp}$ in order to achieve by $RR^{sp}$ and $VT^{sp}$. The inspiration time TI is furthermore fixed.

The pump support system (PSS):

The PSS serves for preventing the fatigue of the patient, who desires a lower $CO_2$-content in his blood, than is achieved by the predefined setting, and therefore actively lifts the respiratory frequency. It regulates the ventilation on account of the active change of the spontaneous respiration rate, and therefore on account of patient behaviour, not on account of a $CO_2$-reading.

Figure 2:
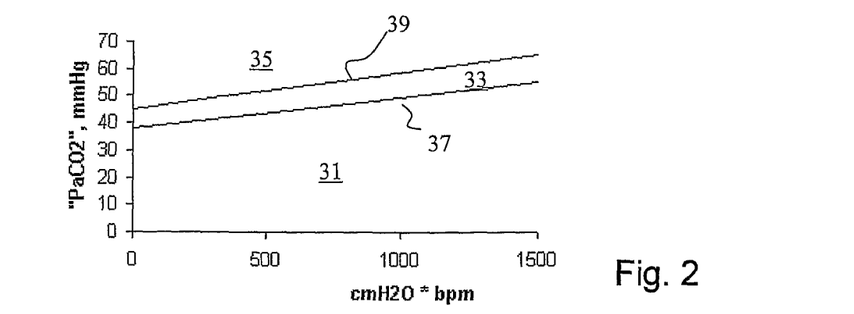
FIG. 2 shows a diagram with two characteristic lines for normal patients.

In a first embodiment, the PSS is designed as follows and has an influence on the CC:

At an interval of in each case 3 minutes, the difference between $RR_{spont}$ minus $RR^{sp}$ is checked. Thereby, a tolerance range of 5 breaths results. If a difference of >5 is ascertained, which is not caused by autotriggering, the ventilation target value $V'_{gA}{}^{SP}$ is increased by the CC by a factor of 1.02. Simultaneously, the lower characteristic line 37 is lowered to "current $PaCO_2^{REP}$-5 mmHg", so that a lower $CO_2$-partial-pressure is assessed as normal. For this reason, the target value $V'_{gA}{}^{SP}$ as a result is not reduced by the CC when $PaCO_2^{REP}$ also drops below the uncorrected lower characteristic line 37. As soon as $RR_{spont}$ again lies above $RR_{sp}$ for 10 minutes within these 5 breaths/min, the characteristic line is then set back again. By way of this, the CC may adapt the target value $V'_{gA}{}^{SP}$ inasmuch as $PaCO_2^{REP}$ gets into the region 31 for values which are too low on account of this shifting of the characteristic line. The tolerance region is increased from 5 to 10 breaths/min with a strategy for withdrawal.

A correction of a ventilation target value or the intensity of the ventilation with the PSS is basically possible independently of whether a representative reading for the arterial $CO_2$-partial-pressure is available or not.

The PSS may therefore also be designed in the following manner, and, if a CC is present, may have no influence on this unless the CC is switched off when the patient breathes in an adequately spontaneous manner, and is switched on when he does not breathe in a sufficiently spontaneous manner.

Figure 6:
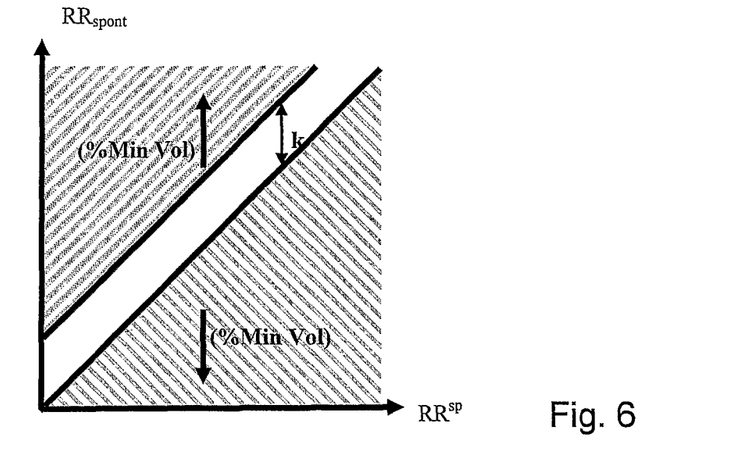
FIG. 6 shows a diagram with the target frequency on the x-axis and the spontaneous frequency on the y-axis and with three regions, which define whether the percent minute volume is lifted, retained or lowered.

The spontaneous frequency is compared to the target frequency over a certain number (e.g. 5, 8, 15 or 30) of consecutive breaths. If thereby, it is ascertained that the spontaneous frequency deviates from the target frequency by a distance value, then depending on this distance value, the % MinVol setting is increased, left alone or reduced. As a distance value within which no change of the % MinVol is carried out, it is suggested to take a fraction or percentage of the percent minute volume, thus of example the set % MinVol divided by 20. At 100% MinVol, the increased frequency results in a difference of up to 5 bpm from the target value, within which region the % MinVol is left unchanged. At 200% MinVol, this region is accordingly 10 bpm wide.

In the diagram according to FIG. 6, the target rate $RR^{sp}$ of the ventilation is plotted on the x-axis and the spontaneous frequency $RR_{spont}$ on the y-axis. The square spanned between both axes is divided into three regions:

A first region extends from the x-axis up to the diagonal through the axis intersection point and includes this diagonal. This diagonal is defined by $RR^{sp}=RR_{spont}$.

A second region borders this diagonal and in the y-direction has an extension k, wherein k may be dependent on the percent minute volume. It may also or alternatively be dependent on the target rate. In any case, this extension k of the second region is advantageously formed in a variable manner.

A third region fills the square between the second region and the y-axis.

Advantageously it is the case: if the spontaneous rate $RR_{spont}$ drops into the first region ($RR_{spont}<$ or $RR^{sp}$), the percent minute volume is reduced under certain circumstances. It may not be reduced if a minimal value (e.g. 100%) has already been reached and/or of the conditions apply, that one may not drop below the initial value defined by the physician, and/or an increase has not yet been carried out. If the spontaneous rate drops into the second region, the presently set percent minute volume is retained. If the spontaneous rate drops into the third region, the percent minute volume is lifted.

If a measurement representative of the arterial $CO_2$-partial-pressure is present, then the characteristic lines of the CC which define the permissible region for the arterial $CO_2$-partial-pressure, may be adapted on account of a deviation of the spontaneous frequency from the target frequency.

A reduction of the % MinVol on account of a comparison of $RR_{spont}$ with $RR^{sp}$ may also need to be carried out only if previously an increase of the % MinVol above a predefined lower limit value has taken place by way of such a comparison.

A reduction of the % MinVol may preferably always be carried out when the following conditions are fulfilled:
% MinVol above 100% and
$RR_{spont}<$ or $=RR^{sp}$.

With a reduction of the % MinVol as a result of a measurement of the $RR_{spont}<$ or $=RR^{sp}$, one may also differentiate as to whether a $CO_2$-measurement is available or not. If no $CO_2$-measurement is available, and if a CC with characteristic lines for the value representative of the arterial $CO_2$-partial-pressure is present, then the characteristic lines of the CC may be lowered. The present measurement value $PaCO_2^{REP}$ which lies in the region 35 as a result of the over-control of the CC by way of the PSS, and would therefore be graded as "too low" by the CC, on account of this, enters between the two characteristic lines into the normal region 33. Thereafter, the reduction of the % MinVol is left to the CC.

Figure 7:
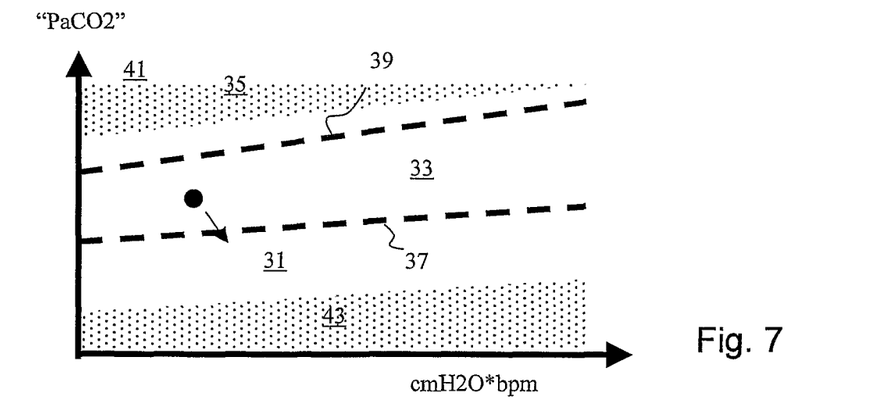
FIG. 7 shows a diagram with the intensity of the ventilation on the x-axis and with the arterial $CO_2$-partial-pressure on the y-axis, and with two characteristic lines for normal patients between two external regions, and with a reading for the $CO_2$-partial-pressure between the two characteristic lines.
Figure 8:
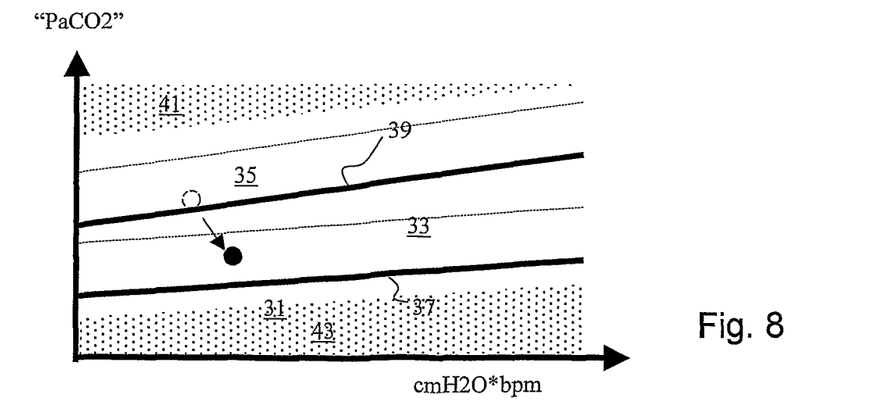
FIG. 8 shows the diagram according to FIG. 7, wherein it is shown that the characteristic lines have been lowered and the intensity of the ventilation has been increased, on account of the spontaneous frequency, with a reading for the $CO_2$-partial-pressure between the two lowered characteristic lines, achieved by way of this.

Characteristic line pairs 37, 39 are represented in FIGS. 7 and 8. These may be displaced within limits in order to meet the requirements of the patient. The displacement is however limited by the extreme regions 41 and 43 which may not fall into the normal region.

An initial position is represented in FIG. 7. It is now assumed that the patient is be ventilated at 130% MinVol at a target rate $RR^{sp}$ of 17 pbm and thereby tires. For this reason, he breathes in a more rapid and shallower manner. The spontaneous rate $RR_{spont}$ lies at 31 bpm for a minute. Since the spontaneous rate over 30 breaths exceeds the target rate $RR^{sp}$ by more than 13 breaths (130% MinVol*mbp/10*10%), the PSS reacts by way of an increase of the % MinVol for example by 10%. By way of this, the intensity of the ventilation (or of the ventilation target value) is increased. The $PaCO_2^{REP}$ drops as a result. A reading would therefore no longer lie within the normal region.

It is to be expected that the limits for an increase of the % MinVol by way of the PSS is no longer achieved subsequent thereto. Assuming that the patient, as a result of his lower arterial $CO_2$-partial-pressure, now reduces the spontaneous rate $RR_{spont}$ to 17 bpm ($=RR_{sp}$) or less, then a reduction of the % MinVol is triggered. The PSS may give rise to the characteristic lines to be lowered according to FIG. 7, until the representative measurement lies in the normal region (FIG. 8), and the reduction of the intensity of the ventilation may be left to the CC. Such an adaptation of the characteristics lines and the transfer to the CC may also be effected as soon as the PSS no longer needs to increase the % MinVol. Then, the over-controlling of the CC by the PSS may be ended, and the adaptation of the ventilation may be left to the CC.

If the patient however breathes in a sufficiently spontaneous manner, then preferably the ventilations continues to be regulated by the PSS.

The adaptation of the % MinVol by the PSS is limited. The PSS may not change the minute volume to below 100%, or, if desired, below the value defined by the CC or by the physician, and for example not to above 250% MinVol.

Figure 9:
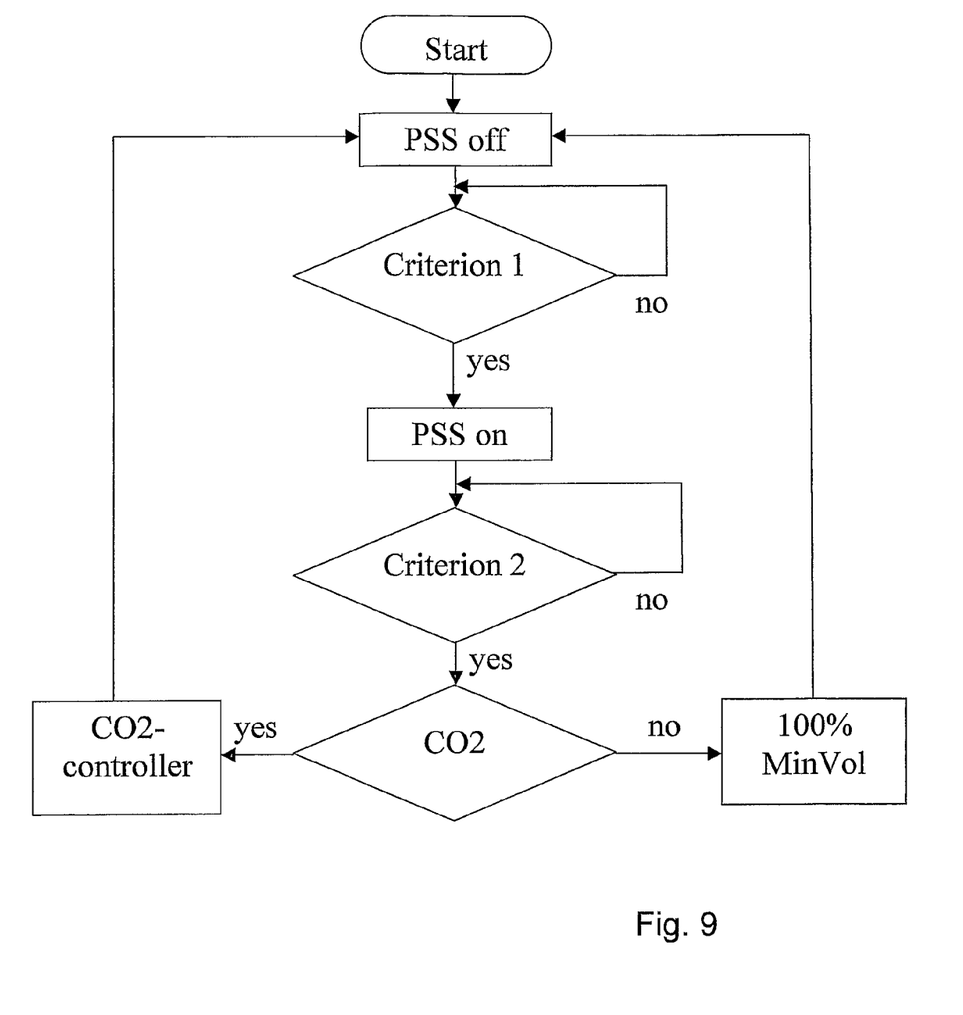
FIG. 9 shows a flow diagram which illustrates the regulation for switching over between a pump support system (PSS)-defined ventilation and a differently determined ventilation.

The flow diagram represented in FIG. 9 illustrates the decision procedures for the connection and disconnection of the PSS in a preferred embodiment If a ventilator provided with a PSS according to the invention is switched on, or the pump support system is switched on, then this is firstly not yet active (block "PSS off"). Prior to this, one ventilates according to a ventilation target value defined by a physician or the CC, and thereby checks as to whether the patient breathes in an adequately spontaneous manner (Rhombus "Criterion 1" between the blocks "PSS on" and "PSS off"). If this criterion is not fulfilled, the PSS remains inactivated (arrow "no" back).

If the criterion is fulfilled, the PSS is activated (block "PSS on"). With an activated PSS, one continuously monitors as to whether the breathing is still effected in a spontaneous manner (Rhombus "Criterion 2"). If it is ascertained that the patient breathes sufficiently spontaneously, then the PSS remains unchanged activated (arrow "no" back). If a switch-off criterion is however fulfilled because the patient no longer breathes sufficiently spontaneously, in order to be able to be applied as a "natural $CO_2$-sensor", one requires a decision. This decision (Rhombus "$CO_2$") is effected on account of the fact as to whether a $CO_2$-measurement is present or not. If no $CO_2$-measurement is present, because the apparatus for example has no $CO_2$-controller or because the $CO_2$ measurement does not function, then the PSS on a safety setting triggers an alarm (display) (arrow "no", block "100% MinVol"). The PSS is then inactivated in its regulating function (block "PSS off"). The safety setting ensures that the patient is ventilated in an adequate if not optimised manner, thus for example with the ventilation target value of 100% MinVol. This setting is then converted from the ASV-controller (or from the ALV-controller) into parameters of the mechanical ventilation which are adequate for the patient. This setting may be changed by the physician whose is called e.g. on account of the alarm. One may envisage the physical setting of the physician being applicable each time when the PSS is inactivated, for a repeated exchange between ventilation target value evaluations determined by the PSS and those determined manually.

If however a $CO_2$-reading and a $CO_2$-controller are present, then this $CO_2$-controller is activated, in order to determine the ventilation target value on account of the $CO_2$-reading. The $CO_2$-controller assumes the task of the PSS, and the PSS is inactivated.

In this operating mode of the ventilator determined by the $CO_2$-controller, one again monitors as to whether the patient breathes sufficiently spontaneously, in order in this case to again activate the PSS and to again deactivate the $CO_2$-controller.

For ascertaining as to whether the patient breathes adequately spontaneously, (criterion 1), in order to activate the PSS, it is compared as to whether a number (e.g. 3) of directly consecutive breaths are effected spontaneously. The time period permissible for this is determined by way of the target frequency $RR^{sp}$.

A difference between the total respiratory frequency and the spontaneous respiratory frequency is monitored for ascertaining as to whether the patient no longer breathes in an adequately spontaneous manner, so that the PSS must be switched off. A predefined number of consecutive breaths (e.g. 8) are monitored, wherein this number is continuously monitored. This means that with each breath, in each case the last for example 8 breaths must be triggered alone by the patient, and may therefore not have any machine-triggered breaths. If this condition is fulfilled at least once within a defined period of time (e.g. one minute), then the PSS remain activated. The PSS is however relieved by a machine or manual evaluation of the ventilation target value geared to a $CO_2$-reading, if this number of directly consecutive spontaneous breaths directly occurs not once within this time period. In other words, if the ventilator within the selected time period within each sequence of the selected number of breaths adds a machine-triggered breath, then a setting of the ventilation target value is applied, which is different to the setting determined by the PSS.

The invention claimed is:

1. A ventilation device for the regulation of a changing intensity of a mechanical ventilation for controlling the respiration of a patient, comprising:
    a mechanical ventilator;
    a circuit coupled with the mechanical ventilator and with a plurality of sensors, said circuit configured for:
    determining a target frequency,
    determining a spontaneous frequency,
    comparing the spontaneous frequency with the target frequency,
    automatically adapting a ventilation target value based on a result of the comparison of the spontaneous frequency with the target frequency, wherein the ventilation target value is a target value for one of a percent minute volume and a total alveolar ventilation,
    adapting parameters determining an intensity of mechanical ventilation, based on the ventilation target value,
    controlling the mechanical ventilator according to the determined intensity of mechanical ventilation, and
    determining the target frequency for a further regulation cycle by automatically setting the target frequency based on the adapted ventilation target value.

2. The device according to claim 1, wherein said circuit is further configured for setting a ventilation pressure or a breath volume based on the adapted ventilation target value.

3. The device according to claim 2, further comprising a controller for matching the parameters determining the intensity of the ventilation pressure or the breath volume, and the ventilation, on account of patient parameters.

4. The device according to claim 1, wherein adapting the ventilation target value increases the ventilation target value when the spontaneous frequency is greater than the target frequency at least by a defined distance value.

5. The device according to claim 1, wherein adapting the ventilation target value reduces the ventilation target value when the spontaneous frequency is smaller than the target frequency.

6. The device according to claim 5, wherein adapting the ventilation target value reduces the ventilation target value when the spontaneous frequency is equal to the target frequency.

7. The device according to claim 4, wherein the distance value is defined depending on a presently set target frequency.

8. The device according to claim 4, wherein the distance value is dependent on a presently measured spontaneous frequency.

9. The device according to claim 4, wherein the distance value is dependent on the intensity of the mechanical ventilation.

10. The device according to claim 4, wherein the distance value is determined as a fraction of a current ventilation target value.

11. The device according to claim 1, wherein adapting the ventilation target value comprises multiplying the ventilation target value by a factor larger than 1 with a breath-wise correction of the ventilation target value, up to about 1.1 with larger correction intervals, when the spontaneous frequency lies above a computed target frequency by a certain number of breaths per minute.

12. The device according to claim 11, wherein said circuit is further configured for temporal control of the adapting the ventilation target value such that the adapting the ventilation target value is activated in a periodic time interval.

13. The device according to claim 11, wherein adapting the ventilation target value is continuously activated and adapt the ventilation target value in a breathwise manner.

14. The device according to claim 1, wherein said circuit is further configured for determining and/or adapting the ventilation target value in a second manner different from a first manner, and is also further configured for switching-over from the first manner to the second manner for adapting the ventilation target value.

15. The device according to claim 14, further comprising a CO2-controller, which incorporates respective, current representative readings into a regulation of the mechanical ventilation, in that a reading is compared to an individual or two characteristic lines, and the mechanical ventilation is changed in a manner such that the reading tendentially approaches the individual characteristic line or is to get between the two characteristic lines.

16. The device according to claim 15, wherein adapting the ventilation target value is based on the comparison of the spontaneous frequency with the target frequency or the reading of the CO2-controller, and assumes the adaptation of the ventilation target value.

17. The device according to claim 16, wherein the individual characteristic line or the two characteristic lines are displaced to such an extent, that the current, representative reading lies on the individual characteristic line, or centrally between the two characteristic lines.

18. The device according to claim 1, wherein adapting the ventilation target value increases the ventilation target value for a total alveolar ventilation, a target value for a minute volume or for the ventilation target value, where the spontaneous frequency has a defined distance to the target frequency.

19. The device according to claim 18, wherein the defined distance is dependent on a therapy goal and/or on the target frequency.

20. The device according to claim 1, wherein said circuit is further configured for regulating or activating the mechanical ventilation according to the parameters.

21. The device according to claim 1, wherein the intensity of the mechanical ventilation or a treatment level is determined by a product of a pressure factor or a volume factor, and a frequency factor of present ventilation settings.

22. The device according to claim 14, further comprising a control loop for activating the first manner for adapting the ventilation target value on account of the result of the comparison of the spontaneous frequency with the target frequency, for monitoring a fulfillment of a first criterion, and for switching from the first manner to the second manner for determining and/or adapting the ventilation target value, for monitoring fulfillment of a second criterion, wherein the second criterion sets lesser demands on spontaneous breathing of the patient than the first criterion.

23. The device according to claim 1, wherein the ventilation target value comprises one of a target value for a total alveolar ventilation, a target value for a minute volume, and a target value for a percentage minute volume.

24. A method adapted for automatic regulation of an intensity of a mechanical ventilation for controlling the respiration of a patient, comprising:
providing a mechanical ventilator;
providing a circuit coupled with the mechanical ventilator and with a plurality of sensors;
determining a target frequency and a spontaneous frequency,
comparing the spontaneous frequency with the target frequency,
automatically adapting a ventilation target value based on a deviation of the spontaneous frequency from the target frequency, wherein the ventilation target value is a target value for one of a percent minute volume and a total alveolar ventilation,
automatically adapting the target frequency based on the adapted ventilation target value and thereby determining the target frequency for a further regulation cycle following the automatic adaptation of parameters determining the intensity of the mechanical ventilation; and
controlling the mechanical ventilator according to the determined intensity of mechanical ventilation.

25. The method according to claim 24, further comprising multiplying the ventilation target value for a total alveolar ventilation, a minute volume or a percent minute volume, by a factor larger than 1, if the spontaneous frequency is above the computed target frequency for more than a certain number of breaths per minute, which is dependent on a presently set ventilation target value.

26. The method according to claim 24, further comprising adapting the ventilation target value on account of the comparison of the spontaneous frequency with the target frequency or on account of a $CO_2$-measurement.

27. The method according to claim 26, further comprising, upon adapting the ventilation target value on account of a representative reading, incorporating a respective current representative reading into a regulation of the mechanical ventilation, in a manner such that the current representative reading is compared to one or two characteristic lines, and the mechanical ventilation is changed in a manner such that the current representative reading tendentially approaches the one characteristic line or comes between the two characteristic lines.

28. The method according to claim 27, further comprising, before adoption of a regulation by the $CO_2$-controller, displacing the one characteristic line or two characteristic lines to such an extent that the current representative reading lies on the individual characteristic line or is centrally between the two characteristic lines.

29. The method according to claim 24, further comprising automatically adapting the ventilation target value, wherein the ventilation target value comprises one of a target value for a total alveolar ventilation, a target value for a minute volume, and a target value for a percentage minute volume.

* * * * *